(12) United States Patent
Sarne

(10) Patent No.: US 10,660,872 B2
(45) Date of Patent: May 26, 2020

(54) METHODS FOR TREATMENT OF COGNITIVE DECLINE

(71) Applicant: Ramot at Tel-Aviv University Ltd., Tel-Aviv (IL)

(72) Inventor: Yosef Sarne, Tel-Aviv (IL)

(73) Assignee: Ramot at Tel-Aviv University Ltd., Tel-Aviv (IL)

(*) Notice: Subject to any disclaimer, the term of this patent is extended or adjusted under 35 U.S.C. 154(b) by 0 days.

(21) Appl. No.: 15/523,934

(22) PCT Filed: Nov. 2, 2015

(86) PCT No.: PCT/IB2015/058453
§ 371 (c)(1),
(2) Date: May 2, 2017

(87) PCT Pub. No.: WO2016/071819
PCT Pub. Date: May 12, 2016

(65) Prior Publication Data
US 2017/0333387 A1 Nov. 23, 2017

Related U.S. Application Data

(60) Provisional application No. 62/074,134, filed on Nov. 3, 2014.

(51) Int. Cl.
*A61K 31/352* (2006.01)
*A61K 31/05* (2006.01)
*A61K 45/06* (2006.01)
*A61K 36/185* (2006.01)
*A61K 9/00* (2006.01)

(52) U.S. Cl.
CPC ............ *A61K 31/352* (2013.01); *A61K 9/006* (2013.01); *A61K 9/0043* (2013.01); *A61K 31/05* (2013.01); *A61K 36/185* (2013.01); *A61K 45/06* (2013.01)

(58) Field of Classification Search
CPC .................................................. A61K 31/352
USPC ......................................................... 514/454
See application file for complete search history.

(56) References Cited

U.S. PATENT DOCUMENTS

| 5,804,592 A | 9/1998 | Volicer | |
|---|---|---|---|
| 2008/0112895 A1 | 5/2008 | Kottayil et al. | |
| 2011/0257256 A1* | 10/2011 | Fuchs | A61K 31/352 514/454 |

FOREIGN PATENT DOCUMENTS

| GB | 2524469 | 9/2015 |
|---|---|---|
| WO | WO 2012/068516 | 5/2012 |

OTHER PUBLICATIONS

Fishbein et al., Experimental Brain Research, 2012, 221(4), 437-448.*
Jack et al, Neurology, 1999, 52(7): 1397-403.*
Valiveti et al. Eur J. Pharm Biopharm, 2007, 65(2): 247-52 (abstract).*
Guidance for Industry, Estimating the Maximum Safe Starting Dose in Initial Clinical Trials for Therapeutics in Adult Healthy Volunteers, U.S. Dept. of Health and Human Services, Food and Drug Administration, CDER, Jul. 2005.
Katsimpardi, et al., Rejuvenation of the Aging Mouse Brain by Young Systemic Factors, Science, 2014, 344, 630-634.
Shannon Reagan-Shaw et al., Dose Translation From Animal to Human Studies Revisited, The FASEB Journal, 2018, 22:3, 659-661.
Saul A. Villeda, et al., Young Blood Reverses Age-Related Impairments in Cognitive Function and Synaptic Plasticity in Mice, Nature Medicine, 2014, 20(6), 659-663.
Cao Chuanhai et al., The Potential Therapeutic Effects of THC on Alzheimer's Disease, Journal of Alzheimer's Disease, 2014, 973-984, vol. 42, No. 3.
Same Y. et al., The dual neuroprotective-neurotoxic profile of cannabinoid drugs, Br. J. Pharmacol., 2011, 1391-401, vol. 163, No. 7.
European Search Report, dated 2018.
Notice of Reasons for Rejection dated Jun. 5, 2019 From the Japan Patent Office Re. Application No. 2017-542498 and Its Translation Into English. (11 Pages).
Supplementary European Search Report and the European Search Opinion dated May 15, 2018 From the European Patent Office Re. Application No. 15856362.7. (7 Pages).
Cao et al. "Potential Therapeutic Effects of THC on Alzheimer's Disease", Journal of Alzheimer's Disease, XP009505129, 42(3): 973-984, 2014.
Sarne et al. "The Dual Neuroprotective-Neurotoxic Profile of Cannabinoid Drugs", British Journal of Pharmacology, XP055278363, 163(7): 1391-1401, Aug. 2011.
Albayram et al. "Loss of CB1 Receptors Leads to Differential Age-Related Changes in Reward-Driven Learning and Memory", Frontiers in Aging Neuroscience, 4(34): 1-8, Published Online Dec. 5, 2012.
Amal et al. "Long-Term Consequences of a Single Treatment of Mice With an Ultra-Low Dose of Delta9-Tetrahydrocannabinol (THC)", Behavioural Brain Research, 206(2): 245-253, Available Online Sep. 18, 2009.
Marchalant et al. "Cannabinoid Receptor Stimulation Is Anti-Inflammatory and Improves Memory in Old Rats", Neurobiology of Aging, 29(12): 1894-1901, Published Online Jun. 11, 2007.
Meier et al. "Persistent Cannabis Users Show Neuropsychological Decline From Childhood to Midlife", Proc. Natl. Acad. Sci. USA, PNAS, 109(40): E2657-E2664, Published Online Aug. 27, 2012.

(Continued)

*Primary Examiner* — Rei Tsang Shiao

(57) ABSTRACT

Embodiments of the invention relate to methods for treatment of age-related cognitive decline in a patient comprising administering to the patient a low dose of tetrahydrocannabinol (THC), preferably in an amount of 10-400 micrograms (μg). THC may be administered in a variety of routes. Methods for delaying or slowing or reversing the progression of age-related cognitive decline using THC are also disclosed. The aforementioned methods may slow the progression of age-related cognitive decline. The cognitive decline may be in a patient suffering from Mild Cognitive Impairment (MCI) or a patient with no MCI, in which cognitive decline is prevented.

21 Claims, 1 Drawing Sheet

(56) References Cited

OTHER PUBLICATIONS

Petersen "Mild Cognitive Impairment as a Diagnostic Entity", Journal of Internal Medicine, 256(3): 183-194, Sep. 2004.
Petersen et al. "Mild Cognitive Impairment: Clincal Characterization and Outcome", Archives of Neurology, 56(3): 303-308, Mar. 1999.
Roberts et al. "The Incidence of MCI Differs by Subtype and Is Higher in Men: The Mayo Clinic Study of Aging", Neurology, 78(5): 342-351, Jan. 31, 2012.
Senn et al. "Long-Term Cognitive Deficits Induced by a Single, Extremely Low Dose of Tetrahydrocannabinol (THC): Behavioral, Pharmacological and Biochemical Studies in Mice", Pharmacology, Biochemistry and Behavior, 88(3): 230-237, Available Online Aug. 23, 2007.
Solowij et al. "Verbal Learning and Memory in Adolescent Cannabis Users, Alcohol Users and Non-Users", Psychopharmacology, 216(1): 131-144, Published Online Feb. 17, 2011.
Tselnicker et al. "A Single Low Dose of Tetrahydrocannabinol Induces Long-Term Cognitive Deficits", Neuroscience Letters, 411(2): 108-111, Published Online Nov. 7, 2006.

* cited by examiner

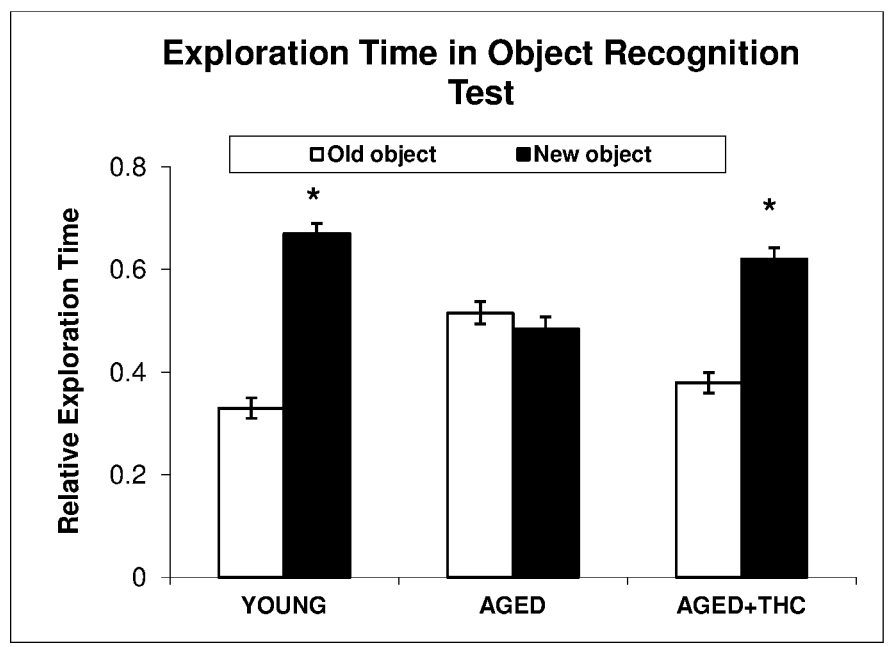

METHODS FOR TREATMENT OF COGNITIVE DECLINE

RELATED APPLICATIONS

The present application claims the benefit under 35 U.S.C. 119(e) of U.S. Provisional Application 62/074,134 filed on Nov. 3, 2014, the disclosure of which is incorporated herein by reference.

TECHNICAL FIELD

Embodiments of the invention relate to methods for treatment of cognitive decline and compositions for the treatment of cognitive decline.

BACKGROUND

Brain aging processes impact multiple systems, cell types and pathways, and often result in cognitive decline and increased risk of Alzheimer's disease (AD). Age-related cognitive decline is typically associated with memory loss, but may be accompanied by symptoms including, but not limited to confusion, impaired judgment, personality changes, disorientation, and loss of language skills. These aging processes are often spontaneous and are not linked to other pathologies or injuries.

Early in aging, in particular in the elderly and typically above 60 years of age mild symptoms of abnormalities in brain function or behavior may develop. Some patients may develop such symptoms earlier, starting in the middle 40's. Patients who have some observed symptoms of cognitive decline but typically perform normal activities in daily life and suffer from no other pathologies, may be diagnosed as suffering from "mild cognitive impairment" (MCI). Patients suffering from MCI in which memory is primarily affected may be considered to suffer from amnestic MCI. Some consider MCI as a prodromal phase, i.e. a phase prior to but on the way towards disease, for example, AD. However, many MCI patients will never proceed to other diseases and will remain MCI patients.

Other types of cognitive decline that may be age-related but associated with other pathologies include AD, Lewy body dementia, vascular dementia, Parkinson's Disease and Huntington's disease.

Various therapeutic approaches to prevention and treatment have been suggested including pharmaceutical intervention, optimization of diet, optimization of sleep, reduction of stress, exercise and brain stimulation. To date, no cure or prevention of age-related cognitive decline has been found to be effective and approved for use. Cholinesterase inhibitors have been administered to patients suffering from dementia associated with AD, but the benefit is slight.

SUMMARY

Embodiments of the invention provide a method for treatment and/or prevention of age-related cognitive decline comprising administering to a patient in need thereof a low dose of Tetrahydrocannabinol (THC). Low doses of THC may be effective in treatment and prevention of age-related cognitive decline, for example memory loss, in elderly patients. Preferably, the low dose is a dose in which the patient does not sense acute side effects. Acute side effects which may be avoided when performing methods according to embodiments of the invention may be selected from the group consisting of: euphoria, sedation, drowsiness, mental clouding, decreased motor coordination and an increase in appetite.

THC, whose main isomer is chemically known as (−)-trans-$\Delta^9$-tetrahydrocannabinol is the main psychoactive constituent of the _Cannabis_ plant. _Cannabis_ is a genus of plants comprising the species _Cannabis sativa, C. indica_, and _C. ruderalis. Cannabis_ plants have been cultivated for a variety of uses including making fibers (hemp), medicinal use and recreational drug use. _Cannabis_ is also commonly known as marijuana.

One of the ways that _Cannabis_ is used for medicinal use in many countries (also known as medical marijuana) is through smoking. Smoking _Cannabis_ is typically performed by using a pipe, by using a water-pipe (also known as a bong) which filters the smoke through water before inhalation or by rolling in paper to form marijuana cigarettes, also known colloquially as "joints." The part of the plant typically used for smoking is the whole flower and budding leaf. When patients self-administer _Cannabis_ through smoking, the patient usually self-titrates the dosage by continuing to smoke until he or she feels a desired change of mood, sense of euphoria or sense of relaxation.

Cannabinoids are compounds active on cannabinoid receptors in humans. Cannabinoids of plant origin, also known as phyto-cannabinoids, are abundant in plants of the _Cannabis_ genus. Two known cannabinoids which are present in relatively high concentrations in _Cannabis_ are THC and cannabidiol (CBD). Psychoactive and other medical effects of many of the cannabinoids have been studied. For example, THC was found to have euphoric effects, analgesic effects, antioxidant effects and to increase appetite. Although individual chemical components of _Cannabis_ have been isolated, many jurisdictions approve the use and sale of medical _Cannabis_ plant matter for a variety of indications.

A pharmaceutical formulation that contains pure THC is known as dronabinol, and can be obtained in oral capsules known as Marinol®. Marinol® has been approved for the treatment of loss of appetite associated with weight loss in patients with AIDS in various countries. Marinol® has also been approved as an anti-emetic in chemotherapy treatment and as an additive analgesic in neuropathic pain.

Isolated THC may be manufactured by isolation from _Cannabis_ plant matter or by chemical synthesis, for example by conversion of another cannabinoid to THC.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF FIGURES

FIG. 1 describes a bar graph showing an object recognition test result, in indication of memory, relating to relative exploration time of a "new object" and an "old object" presented to mice in a young, control group, an untreated aged mice group, and an aged mice group treated with low dose THC, in which memory is significantly improved relative to untreated aged mice as evident by significantly longer exploration of a new object compared to the old object.

DETAILED DESCRIPTION

Use of cannabinoids at conventional doses, which are equivalent to doses in rodents of about 1 to about 20 milligrams/kilogram (mg/kg) induce conventional somatic and psychotropic effects of cannabinoids, including slowing down of motor and mental activity. When such conventional doses of cannabinoids including THC are chronically administered to rodents they induced long term cognitive impairments that are accompanied by degenerative processes in the brain.

In humans, a single exposure to a conventional dose of *Cannabis* (marijuana) impairs mental abilities for several hours (depending on the administered dose) while chronic exposure to conventional doses of cannabinoids results in long lasting cognitive deficits, manifested as impairment in attention, motivation, memory or executive functions. MRI studies showed a reduction in white and gray matter in the brains of chronic heavy *Cannabis* users.

The inventor has surprisingly found that administration of doses which are significantly lower than conventional doses has the opposite effect of administration of conventional doses. In addition, administration of such low doses were shown to treat age-related cognitive decline in a rodent model performed in aged mice. Administration of low doses which does not induce acute measurable somatic and/or psychotropic effects has been shown by the inventor and described in further detail herein below to treat and reverse age-related memory decline. Intermittent administration of low doses for about 3 weeks was shown to be sufficient to provide long term effects on age-related cognitive decline in mice. It is suggested that administration of even a single low dose may be effective in providing similar long term effects.

Conventional doses may be represented by the amount of THC administered upon smoking *Cannabis* and self-titration by the user continuing to smoke until he or she feels a desired change of mood, sense of euphoria or sense of relaxation. Users of *Cannabis* who administer by smoking self-administer between about 2 mg and about 20 mg per smoking session. Some users may self-administer between once and several times per day. Additionally, conventional doses of THC in the form of dronabinol capsules are available in doses of 2.5, 5 or 10 mg.

The oromucosal spray nabiximols, (marketed under the trade name Sativex® and authorized in various countries for treating Multiple Sclerosis Spasticity) comprises THC and Cannabidiol, in an amount of 2.7 mg of THC per spray. Patients administer about 4-12 sprays daily. This too represents a conventional dosing of THC.

As shown in greater detail below, mouse models in aged mice showed that untreated, aged mice suffer from decreased memory relative to young mice. When aged mice were treated with low doses of THC, at 0.002 mg/kg, the aged mice displayed memory improvement to the extent that their memory tested similarly to young mice.

The dose shown by the inventor to be effective in mice is equivalent to a dose in humans of about 0.2 micrograms per kilogram (µg/kg) to about 8 µg/kg. In an average human weighing 70 kilograms (kg) this is equivalent to a dose of about 10-400 micrograms (µg). Conversion of animals doses to human doses is based on body surface area normalization, as suggested by FDA guidelines.

According to an embodiment of the invention, a method for treatment of age-related cognitive decline in a patient is provided, in which the patient is administered a low dose of between about 10-400 µg of THC. According to an embodiment, the amount administered is between 10-100 µg. According to an embodiment, the amount administered is between 10-20 µg.

According to an embodiment of the invention, the patient is administered a low dose of THC once daily, 3 times per week, or once per week. According to an embodiment of the invention, the length of treatment may be one day, about three weeks or about one month. According to an embodiment of the invention, a patient is assessed for symptoms of age-related cognitive decline after a treatment regimen, and may be subsequently re-administered THC upon reassessment.

The pharmaceutical compositions according to an embodiment of the invention are conveniently presented in unit dosage form and are prepared by any of the methods well known in the art of pharmacy. In an embodiment of the invention, the unit dosage form is in the form of a tablet, capsule, lozenge, wafer, patch, ampoule, vial, spray, metered-dose inhaler, sublingual or buccal drops, suppository or pre-filled syringe.

In an embodiment of the invention, the dosage form is solid plant matter configured for smoking or vaporization. In an embodiment of the invention, the solid plant matter may be formed into an extract which is administered, for example through the sublingual route or via parenteral route.

The compositions of the present invention may be administered in the form of a pharmaceutical composition comprising at least one active component together with a pharmaceutically acceptable carrier or diluent.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tableting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the components of this invention can be combined with various sweetening agents, flavoring agents, coloring agents, emulsifying agents and/or suspending agents, as well as such diluents as water, ethanol, propylene glycol, glycerin and various like combinations thereof.

The compositions according to embodiments of this invention may also be administered in a controlled release formulation such as a slow release or a fast release formulation. Such controlled release dosage composition may be prepared using methods well known to those skilled in the art.

For purposes of parenteral administration, solutions in sesame or peanut oil or in aqueous propylene glycol can be employed, as well as sterile aqueous solutions of the corresponding water-soluble salts. Such solutions may be suitably buffered, if necessary, and the liquid diluent first rendered isotonic with sufficient saline or glucose. These solutions are especially suitable for intravenous, intramuscular, subcutaneous and intraperitoneal injection purposes.

Pharmaceutical compositions according to embodiments of the invention may contain an active amount of 0.0000001%-10% of THC.

Pharmaceutical compositions according to embodiments of the invention may be formulated in non-aqueous solutions, optionally encapsulated in soft-gelatin capsules. The soft-gelatin capsule formulations may further comprise one or more than one of the following excipients: glycerin and sesame oil.

Pharmaceutical compositions comprising THC can be prepared as disclosed in U.S. Pat. Nos. 8,603,515; 8,476,312; 7,648,696; 6,730,330; 6,509,005; incorporated herein by reference. Exemplary compositions may be in the form of a pump-action spray for buccal administration. The compositions may comprises a solvent and a co-solvent in combination, wherein the solvent is an alcohol and the co-solvent is selected from the group consisting of glycols, sugar alcohols, carbonate esters and chlorinated hydrocarbons.

Exemplary compositions may be prepared using an alcohol as a solvent, with the addition of carbonic acid. Exemplary compositions may be prepared for inhalation to the lungs, comprising a semiaqueous solvent comprising an alcohol, water and a glycol. Optionally, volumetric ratios of ethanol:water:propylene glycol may be selected from those in the range of from 10-70:10-30:20-80, respectively.

Exemplary compositions may be prepared for administration via a mucosal surface and may comprise a solubilizing agent selected from the group consisting of glycerol monooleate, glycerol monostearate, medium chain triglycerides, polyethoxylated castor oil, polyoxyethylene alkyl ethers, polyoxyethylene ethers, polyoxyetyhlene fatty acid esters, polyoxyothylene stearates and sorbitan esters.

Exemplary compositions may be prepared for administration via a metered dose inhaler and may comprise 1,1,1,2,3,3,3-heptafluoropropane and an organic solvent. Some embodiments of the invention relate to treatments as monotherapy, in which low dose THC is a sole active pharmaceutical agent used to treat a disease. Some embodiments of the invention relate to combination therapies in which low dose THC is used in combination with another active pharmaceutical agent to treat a disease. "In combination with" refers to both drugs being substantially effective in the body at a same time. Both drugs can be administered substantially at the same time, or both drugs can be administered at different times but have effect on the body at the same time.

According to an embodiment of the invention, a method for treatment of age-related cognitive decline is provided in which low dose THC is administered in combination with at least one additional cannabinoid. According to an embodiment of the invention, the additional cannabinoid is CBD. According to an embodiment of the invention, THC and CBD are administered in combination, without the addition of any other cannabinoids.

According to an embodiment of the invention, a method for treatment of age-related cognitive decline is provided in which low dose THC is administered without any additional cannabinoid.

According to an embodiment of the invention, a method for treatment of age-related cognitive decline is provided in which low dose THC is administered in the form of *Cannabis* plant matter. According to an embodiment, the plant matter is administered through inhalation following combustion or vaporization.

According to an embodiment of the invention, a method for treatment of age-related cognitive decline is provided in which low dose THC is administered topically, systemically, or locally. THC may be administered via intravenous, subcutaneous or intramuscular injection. THC may be administered via inhalation or insufflations. THC may be administered via the oral, buccal, sublingual, transdermal, nasal, rectal or parenteral routes.

According to an embodiment of the invention, a method for treatment of age-related cognitive decline is provided in which low dose THC is administered to a patient aged 45 or older. According to an embodiment of the invention, a method for treatment of age-related cognitive decline is provided in which low dose THC is administered to a patient aged 50 or older. According to an embodiment of the invention, a method for treatment of age-related cognitive decline is provided in which low dose THC is administered to a patient aged 55 or older. According to an embodiment of the invention, a method for treatment of age-related cognitive decline is provided in which low dose THC is administered to a patient aged 60 or older. According to an embodiment of the invention, a method for treatment of age-related cognitive decline is provided in which low dose THC is administered to a patient aged 65 or older. According to an embodiment of the invention, a method for treatment of age-related cognitive decline is provided in which low dose THC is administered to a patient aged 70 or older. According to an embodiment of the invention, a method for treatment of age-related cognitive decline is provided in which low dose THC is administered to a patient aged 75 or older.

According to an embodiment of the invention, a method for treatment of age-related cognitive decline is provided in which low dose THC is administered to a patient showing no signs of Alzheimer's disease pathology.

According to an embodiment of the invention, a method for treatment of age-related cognitive decline is provided in which low dose THC is administered to a patient showing signs of AD pathology.

AD pathology may be determined by a physician medical examination, a clinical dementia rating, a MiniMental State Exam, an imaging scan such as Positron Emission Tomography (PET) scan or any combination of these methods.

According to an embodiment of the invention, a method for treatment of age-related cognitive decline is provided in which low dose THC is administered to a patient who has not experienced stroke.

According to an embodiment of the invention, a method for treatment of age-related cognitive decline is provided in which low dose THC is administered to a patient who has not experienced traumatic brain injury.

According to an embodiment of the invention, a method for treatment of age-related cognitive decline is provided in which low dose THC is administered to a patient who has not experienced epileptic seizures.

According to an embodiment of the invention, a method for treatment of age-related cognitive decline is provided in which a patient suffering from or at risk of age-related cognitive decline is administered low dose THC, thereby halting progression of cognitive decline. According to an embodiment of the invention, the progression of cognitive decline is evaluated by one or more of Clinical Dementia Rating (CDR) and MiniMental State Exam (MMSE).

Without being bound by theory, it is suggested that a low dose of THC can activate extracellular signal-regulated kinases (ERK), cAMP response element-binding protein (CREB) and brain-derived neurotrophic factor (BDNF) in a patient administered the dose and may protect the patient's brain from age-related deterioration and may even reverse age-related cognitive deficits.

Example 1a: Testing Memory after Administration of Low-Dose THC in Aged Mice Using an Object Recognition Test Three groups of ICR female mice, having 10 mice in each group, were used for this test. Test mice aged fifteen months old (aged mice) were injected with 0.002 mg/kg THC, through the intraperitoneal route, 3 times a week for three weeks. A THC solution was prepared by dissolving a stock solution of 100 mg/ml THC in ethanol into a vehicle solution consisting of ethanol:cremophor:saline in a 1:1:18 ratio. THC was diluted to the appropriate dosage and administered in a volume of injection of 0.1 ml per 10 g of mouse body weight. Two groups of mice were used as control. One control group comprised 10 young mice, aged 8 weeks, treated with vehicle without THC. Another control group comprised 10 aged mice that were treated with vehicle without THC. No adverse acute effects were recognized upon administration. Three weeks after the last administration, the cognitive ability of the mice was tested by the Object Recognition Test, a behavioral assay that measures visual memory, based on the natural tendency of mice to explore novel objects. In the first day of the experiments, the mice were familiarized with two objects in the experimental arena. The mice did not dissociate between the two objects and spent similar time in exploring each of them. Twenty-four hours later, the mice were introduced to the same arena with one of the familiarized objects replaced by a novel object. Control young mice (YOUNG) remembered the old object and preferred to explore the novel object, as was expressed by statistically significant longer exploration time of the new object relative to the old object. Untreated aged mice (AGED) lost this ability and did not spend more time exploring the new object than the old object, indicating that they had failed to remember the old object. Aged mice treated with low dose THC (AGED+THC), expressing similar behavior as the young control mice, spent significantly more time exploring the new object relative to the old object, indicating that they had remembered the old object. The results, in terms of relative exploration time for each group are shown in FIG. 1. Relative exploration time equals exploration time for a given object, divided by exploration time of both objects.

This model in mice indicates that low doses of THC are effective in restoring memory impacted by cognitive decline in aged mice to a level similar to mice unaffected by age-related cognitive decline.

In comparable low doses in humans, THC may be administered to restore memory in patients suffering from age-related cognitive decline.

Example 1b: Testing Unwanted Side Effects of THC in Conventional Dosages Versus Low Doses ICR mice, six in each group, were administered a single dose of a conventional dose of THC (1, 2 or 10 mg/kg) or a low dose of THC (0.001, 0.002 or 0.01 mg/kg) through the intraperitoneal route, formulated using the method described in example 1a, with dilution to the appropriate dosage. Tests were then performed, starting 15 minutes after injection. Animals were tested for analgesia associated with the conventional doses of THC and the low doses of THC using a "hot plate test" in which animals were placed within a transparent glass cylinder on a hotplate maintained at 45° C. Animals were observed to determine time until reacting to pain caused by the hotplate as indicated by licking or jumping. Animals were tested for hyperthermia associated with administration of conventional doses of THC and the low doses of THC using a rectal thermometer. Animals were tested for immobility associated with conventional doses of THC and the low doses of THC using an open field test. In the open field test, animals were placed in an arena for five minutes, and animal activity was measured. In addition, number of rearings performed during the five minutes was recorded.

All of the conventional doses induced conventional acute cannabinoid effects of THC in the mice including analgesia, hypothermia and immobility. Low doses of THC (0.001, 0.002 and 0.01 mg/kg) failed to induce any of these effects.

As can be seen from the models performed using conventional doses and low doses in mice, analgesia (longer latency to respond to noxious stimulus), reduced body temperature and slowing of motor activity did not occur when treating mice with low doses. It can be assumed from these models that use of equivalent dosages in humans (10-400 µg) can be dosed at regular intervals, for extended periods of time and will not cause acute negative side effects in humans such as slowing of motor and mental activity. Euphoria, change in heart rate and blood pressure, drowsiness, mental clouding, decreased motor coordination and stimulated appetite (often seen in high doses), are not expected to present in humans in which the low dose is administered.

Example 1c: Behavioral Testing of Mice Administered Low Dose of THC

Young ICR mice, at about 8-12 weeks old, and aged ICR mice, about 15 months old, weighing about 30-40 grams each, are housed in standard conditions with free access to food and water. Mice are habituated to handling and injections by daily intraperitoneal injections of saline, at least 4 times prior to treatment.

A THC solution is prepared by dissolving a stock solution of 100 mg/ml THC into a vehicle solution consisting of ethanol:cremophor:saline in a 1:1:18 ratio. THC is administered in a volume of injection of 0.1 ml per 10 g of mouse body weight. The THC concentration administered is 0.002 mg/kg.

Four groups of mice are tested. Young mice, aged 8-12 weeks old injected with either vehicle or THC; aged control mice, which are injected with vehicle alone; and aged test mice, which are injected with 0.002 mg/kg of THC. In each group, 8-12 mice are used. Each group is injected with either vehicle or THC for three times a week for three weeks prior to testing.

Cognitive defects are tested in all four groups using an oasis maze test. The oasis maze is a land-based spatial learning assay. The maze consists of a white plastic arena, 200 cm in diameter, with 20 wells arranged in 3 concentric circles. Each well contains 0.25 ml of water. The maze is situated in a room that contains various visual clues. The mice are allowed to drink freely for only 1 hour per day starting from three days before the experiment and throughout the experiment. Each experiment comprises two parts. In the first part, the training phase, which begins at least 1 week after the last THC or vehicle injection, all wells are filled with water. A mouse is introduced into the arena at different starting points, with its head turned towards a wall of the arena, and the time it takes a mouse from when it is introduced into the arena until it finds and drinks from a well is recorded. The training phase consists of 3 trials of 3 minutes each. During the second part of the experiment, the test phase, a mouse is introduced into the same arena, but now only one of the 20 wells is filled with water, the same well being filled during each of the trials. Each mouse is introduced into the arena twice daily and the arena is cleaned with alcohol after each trial. The time it takes each mouse to locate the single filled well and drink from it is recorded for 8 trials for each mouse.

Upon performance of this experiment the results may show that during the first training phase, young mice from both the vehicle and THC groups quickly develop a strategy for finding the filled well. In the subsequent test phase, the establishment of spatial memory enables the young mice to decrease time to finding the filled well. Time to finding the filled well subsequently decreases over time. In test phase, aged mice treated with vehicle alone do not significantly decrease time to finding the filled well, indicating impaired spatial memory due to age-related cognitive decline. It is suggested that aged mice treated with low dose THC in test trials find the filled well in significantly less time than aged mice treated with vehicle alone. Aged mice treated with low dose THC may perform similarly to young mice in the test trials. This may indicate that low dose THC can be effective in enhancing spatial learning and memory caused as a result of age-related cognitive decline.

Example 1d: Testing Memory after Administration of Low-Dose THC in Combination with CBD in Aged Mice Using an Object Recognition Test Three groups of ICR female mice, having 10 mice in each group, were used for this test. Test mice aged fifteen months old (aged mice) were injected with 0.002 mg/kg THC in combination with 5 mg/kg of CBD through the intraperitoneal route, 3 times a week for three weeks. A THC/CBD solution was prepared by dissolving a stock solution of 100 mg/ml THC and of 100 mg/ml CBD in ethanol into a vehicle solution consisting of ethanol:cremophor:saline in a 1:1:18 ratio. THC and CBD were diluted to the appropriate dosage and administered in a volume of injection of 0.1 ml per 10 g of mouse body weight. Two groups of mice were used as control. One control group comprised 10 young mice, aged 8 weeks, treated with vehicle without THC/CBD. Another control group comprised 10 aged mice that were treated with vehicle without THC/CBD.

The animals were kept and tested as described in example 1a.

The aged mice treated using THC/CBD were shown to have memory similar to the young mice tested. Aged mice treated using THC/CBD may have improved memory relative to aged mice administered with low-dose THC alone.

Example 2: Clinical Trial of THC in Humans Suffering from Age-Related Cognitive Decline About 100 patients having MCI are entered into the trial. Patients are admitted according to the following criteria: 1. Age from 50 to <85 years old. Weight between 60 and 90 kg. 2. Diagnosis of Mild Cognitive Impairment, Amnestic type (single or multi domain) according to Petersen criteria and supported by a Clinical Dementia Rating (CDR) score of about 0.5. 3. Mini-Mental State Examination (MMSE) score of 24-30, inclusive. 4. Ability to attend all clinical visits and have an informant capable of accompanying the subject on specific clinic visits for two years or the duration of the study. 5. Adequate manual dexterity, visual, and auditory abilities to perform all aspects of the cognitive and functional assessments.

The trial is double-blinded. Patients are randomly split into 3 treatment groups and a placebo group, according to the schedule in table 1.

TABLE 1

| Group | Treatment and Frequency |
| --- | --- |
| Placebo | Placebo, once daily or once weekly |
| Treatment #1 | 100 micrograms, once daily via sublingual administration for four weeks |
| Treatment #2 | 100 micrograms, once a week, sublingual, for four weeks |
| Treatment #3 | 100 micrograms, once a week, sublingual, continuous until the end of the trial |

Each patient is analyzed at baseline and at 2, 8, 16, and 24 months after initiation of administration of treatment regimen or placebo. Analysis assesses for change in cognitive performance measured by MMSE and CDR.

It is suggested that over the course of the treatment of groups 1-3, THC may be successful in slowing or halting the decline of cognitive performance in MCI patients, as measured by MMSE and CDR. In some patients, decline of cognitive performance may even be reversed. In addition, it is suggested that in treatment groups 1-3, progression to AD may be evident to a lesser degree than in placebo group.

There is further provided in accordance with an embodiment of the invention a method for the treatment of age-related cognitive decline in a patient comprising administering to the patient tetrahydrocannabinol (THC) in an amount of 10-400 micrograms (µg). There is further provided in accordance with an embodiment of the invention a method for delaying or slowing the progression of age-related cognitive decline in a patient comprising administering to the patient tetrahydrocannabinol (THC) in an amount of 10-400 micrograms (µg). Optionally, the patient suffers from mild cognitive impairment (MCI). Optionally, the MCI is amnestic MCI. Optionally, the age-related cognitive decline relates to decline in memory. Optionally, the administration slows the progression of age-related cognitive decline as determined by Clinical Dementia Rating or MiniMental State Exam. Optionally, the dose is less than or equal to 100 µg. Optionally, the dose is less than or equal to 20 µg. Optionally, the THC is administered on a daily basis. Optionally, THC is administered between 2 and 6 times per week. Optionally, THC is administered once per week. Optionally, THC is administered through a pharmaceutical composition comprising at least one excipient. Optionally, THC is administered through a route selected from the group consisting of: topical, systemic, local, intravenous, subcutaneous, intramuscular, inhalation, insufflation, oral, buccal, sublingual, transdermal, nasal, rectal and parenteral routes. Optionally, THC is administered in combination with another active pharmaceutical agent. Optionally, THC is administered in combination with at least one additional cannabinoid. Optionally, the cannabinoid is cannabidiol (CBD). Optionally, THC is administered in the absence of an additional cannabinoid. Optionally, THC is administered in the form of extracted, combusted or vaporized *Cannabis* plant matter. Optionally, the patient is greater than or equal to 45 years old. Optionally, the patient is greater than or equal to 50 years old. Optionally, the patient is greater than or equal to 55 years old. Optionally, the patient is greater than or equal to 60 years old. Optionally, the patient is greater than or equal to 65 years old. Optionally, the patient is greater than or equal to 70 years old Optionally, the patient is greater than or equal to 75 years old. Optionally, the patient exhibits signs of Alzheimer's Disease (AD) pathology. Optionally, the patient exhibits no signs of AD pathology. Optionally, the patient has not experienced a stroke in the month prior to administration of the THC. Optionally, the patient has not experienced traumatic brain injury in the month prior to administration of the THC. Optionally, the patient has not experienced epileptic seizure in the month prior to administration of the THC. Optionally, THC is administered chronically for a period of about one month. Optionally, THC is administered chronically for a period of at least one year. Optionally, THC is administered in a single treatment. There is further provided in accordance with an embodiment of the invention a method for the improvement of cognitive functioning in aged patients comprising administering to the patient tetrahydrocannabinol (THC) in an amount of 10-400 μg of THC.

There is further provided in accordance with an embodiment of the invention a method for the manufacture of a medicament for the treatment of age-related cognitive decline, the medicament comprising an amount of 10-400 μg of THC. There is further provided in accordance with an embodiment of the invention pharmaceutical composition for the treatment of age-related cognitive decline comprising an amount of 10-400 μg of THC.

There is further provided in accordance with an embodiment of the invention a pharmaceutical composition in unit dose form comprising between 10 and 400 μg of THC. Optionally, the dosage form is in the form of a tablet, capsule, lozenge, wafer, patch, ampoule, vial, spray, metered-dose inhaler, sublingual or buccal drop, suppository or pre-filled syringe.

In the description and claims of the present application, each of the verbs, "comprise," "include" and "have," and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A method for treatment of mild cognitive impairment (MCI) in a patient comprising administering to the patient tetrahydrocannabinol (THC) in an amount of 20-400 micrograms (μg), wherein the patient is at least 45 years old, and has not experienced a stroke, traumatic brain injury or an epileptic seizure in the month prior to administration of the THC.

2. The method according to claim 1, wherein the treatment comprises delaying or slowing the progression of mild cognitive impairment.

3. The method according to claim 1, wherein the MCI is amnestic MCI.

4. The method according to claim 1, wherein the THC is administered in an amount between 20 and 100 μg.

5. The method according to claim 1, wherein the THC is administered in an amount between 20 and 300 μg.

6. The method according to claim 4, wherein the THC is administered on a daily basis.

7. The method according to claim 4, wherein the THC is administered at least once per week.

8. The method according to claim 1, wherein the THC is administered in a pharmaceutical composition comprising at least one excipient.

9. The method according to claim 1, wherein the THC is administered through a route selected from the group consisting of: topical, systemic, local, intravenous, subcutaneous, intramuscular, inhalation, insufflation, oral, buccal, sublingual, transdermal, nasal, rectal and parenteral routes.

10. The method according to claim 1, wherein the THC is administered in combination with at least one additional active pharmaceutical agent.

11. The method according to claim 10, wherein the at least one additional active pharmaceutical agent is a cannabinoid.

12. The method according to claim 11, wherein the cannabinoid is cannabidiol (CBD).

13. The method according to claim 12, wherein the CBD is administered in an amount of between 2 and 20 milligrams.

14. The method according to claim 13, wherein the CBD is administered in an amount of 5 milligrams.

15. A method for the improvement of cognitive functioning in a patient comprising administering to the patient tetrahydrocannabinol (THC) in an amount of 20-400 μg of THC, wherein the patient is at least 45 years old, and has not experienced a stroke, traumatic brain injury or an epileptic seizure in the month prior to administration of the THC.

16. The method according to claim 1, wherein the THC is administered in an amount of 300-400 μg.

17. The method according to claim 9, wherein the THC is administered sublingually.

18. The method according to claim 9, wherein the THC is administered nasally.

19. The method according to claim 15, wherein the THC is administered in an amount of 300-400 μg.

20. The method according to claim 15, wherein the THC is administered in a pharmaceutical composition comprising at least one excipient.

21. The method according to claim 15, wherein the THC is administered through a route selected from the group consisting of: topical, systemic, local, intravenous, subcutaneous, intramuscular, inhalation, insufflation, oral, buccal, sublingual, transdermal, nasal, rectal and parenteral routes.

* * * * *